United States Patent
Merkel et al.

(10) Patent No.: US 10,843,927 B2
(45) Date of Patent: Nov. 24, 2020

(54) ENERGY-EFFICIENT METHOD FOR PROVIDING A PURIFIED PHOSGENE VAPOR

(71) Applicant: Covestro Deutschland AG, Leverkusen (DE)

(72) Inventors: Michael Merkel, Düsseldorf (DE); Martin Ehrig, Leverkusen (DE); Manfred Kobylka, Burscheid (DE); Jan Morbach, Cologne (DE); Maria Carrascosa Mas, Cologne (DE); Christian Morten Jens, Cologne (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/621,944

(22) PCT Filed: Jun. 22, 2018

(86) PCT No.: PCT/EP2018/066746
§ 371 (c)(1),
(2) Date: Dec. 12, 2019

(87) PCT Pub. No.: WO2019/002121
PCT Pub. Date: Jan. 3, 2019

(65) Prior Publication Data
US 2020/0180965 A1 Jun. 11, 2020

(30) Foreign Application Priority Data
Jun. 29, 2017 (EP) .................................. 17178652

(51) Int. Cl.
| | | |
|---|---|---|
| C01B 32/80 | (2017.01) | |
| B01D 1/00 | (2006.01) | |
| B01D 5/00 | (2006.01) | |
| B01J 19/00 | (2006.01) | |
| C07C 263/10 | (2006.01) | |

(52) U.S. Cl.
CPC ............ *C01B 32/80* (2017.08); *B01D 1/0011* (2013.01); *B01D 1/0082* (2013.01); *B01D 5/006* (2013.01); *B01D 5/0051* (2013.01); *B01D 5/0093* (2013.01); *B01J 19/0013* (2013.01); *C07C 263/10* (2013.01); *B01J 2204/005* (2013.01); *B01J 2219/00076* (2013.01); *B01J 2219/00162* (2013.01)

(58) Field of Classification Search
CPC ...... C07C 53/46; B01D 1/2856; B01D 3/007; B01D 3/02; B01D 3/101; C01B 32/80
See application file for complete search history.

(56) References Cited

U.S. PATENT DOCUMENTS

| | | | |
|---|---|---|---|
| 3,226,410 A | 12/1965 | Hettich et al. | |
| 4,231,959 A * | 11/1980 | Obrecht | C01B 32/80 562/847 |
| 4,681,661 A * | 7/1987 | Govind | B01D 3/04 202/154 |
| 4,764,308 A * | 8/1988 | Sauer | C01B 32/80 562/847 |
| 4,847,408 A | 7/1989 | Frosch et al. | |
| 4,943,426 A * | 7/1990 | Dastolfo, Jr. | C01F 5/32 423/497 |
| 5,449,818 A | 9/1995 | Biskup et al. | |
| 6,022,993 A * | 2/2000 | Cicha | C01B 32/80 562/847 |
| 6,225,497 B1 * | 5/2001 | Becker | B01F 5/0256 560/347 |
| 6,719,957 B2 * | 4/2004 | Brady, Jr. | B01D 53/002 423/240 R |
| 6,803,483 B2 * | 10/2004 | Lokum | C07C 263/20 560/347 |
| 7,442,835 B2 * | 10/2008 | Keggenhoff | B01J 8/0085 562/847 |
| 7,524,405 B2 * | 4/2009 | Sohn | C07C 263/20 203/27 |
| 7,584,629 B2 * | 9/2009 | Sohn | C01B 7/0712 558/270 |

(Continued)

FOREIGN PATENT DOCUMENTS

| | | | | |
|---|---|---|---|---|
| EP | 0134506 A2 * | 3/1985 | ............ | C01B 32/80 |
| WO | 2012110597 A1 | 8/2012 | | |

(Continued)

OTHER PUBLICATIONS

English-Language Machine Translation of WO 2012/130788 (2012) (Year: 2012).*
B. de Jong et al., Phosgene Production from Carbon Monoxide Separated from Steel Industry Flue Gas and Chlorine (2018) (Year: 2018).*
K. Dunlap, Phosgene in, Kirk-Othmer Encyclopedia of Chemical Technology (2010) (Year: 2010).*

(Continued)

*Primary Examiner* — Alexander R Pagano
(74) *Attorney, Agent, or Firm* — John E. Mrozinski, Jr.

(57) ABSTRACT

The present invention relates to a method for producing purified phosgene vapor, comprising the following steps: 1) providing a gas flow obtainable from the reaction of chlorine with carbon monoxide and comprising phosgene and carbon monoxide; 2) one-stage or multi-stage condensation of the gas flow and separation of non-condensable residue gases; 3) one-stage or multi-stage evaporation of the liquid phosgene obtained in step 2) and optional overheating of the produced phosgene vapour, wherein there is an energy integration between one or more of the condensation steps of step 2) and one or more of the evaporation steps in step 3) and the pressure in the last condensation step is between ≥0.2 and ≤6.0 bar higher than in the first evaporation step.

14 Claims, 6 Drawing Sheets

(56) References Cited

U.S. PATENT DOCUMENTS

| | | | | |
|---|---|---|---|---|
| 7,612,234 B2* | 11/2009 | Haas | ...................... | B01D 53/62 |
| | | | | 562/847 |
| 8,993,803 B2* | 3/2015 | Olbert | ...................... | C01B 32/80 |
| | | | | 562/848 |
| 9,023,300 B2* | 5/2015 | Olbert | ...................... | B01J 8/067 |
| | | | | 422/652 |
| 9,751,768 B2* | 9/2017 | Mouazer | ............... | C07C 263/20 |
| 10,252,912 B2* | 4/2019 | Schelling | ................ | C01B 32/80 |
| 2002/0065432 A1* | 5/2002 | Eckert | ...................... | C01B 32/80 |
| | | | | 562/847 |
| 2003/0233013 A1 | 12/2003 | Lokum et al. | | |
| 2005/0118088 A1* | 6/2005 | Olbert | ................ | B01J 19/0053 |
| | | | | 423/416 |
| 2006/0047170 A1* | 3/2006 | Keggenhoff | ........... | B01J 8/0085 |
| | | | | 562/847 |
| 2006/0123842 A1 | 6/2006 | Sohn et al. | | |
| 2007/0003477 A1* | 1/2007 | Haik-Beraud | ....... | B01D 53/864 |
| | | | | 423/650 |
| 2007/0051238 A1* | 3/2007 | Jain | .......................... | C10K 1/32 |
| | | | | 95/96 |
| 2007/0276158 A1* | 11/2007 | Haas | ...................... | B01D 53/62 |
| | | | | 562/847 |
| 2009/0143619 A1* | 6/2009 | Kauth | ...................... | B01J 8/067 |
| | | | | 562/847 |
| 2012/0048711 A1* | 3/2012 | Werba | ................... | C07C 5/2732 |
| | | | | 202/158 |
| 2012/0267076 A1* | 10/2012 | Yang | ................... | B01D 1/0058 |
| | | | | 165/104.19 |
| 2017/0101367 A1* | 4/2017 | Knauf | ................... | B01J 12/005 |
| 2018/0044179 A1* | 2/2018 | Schelling | .............. | C01B 7/0712 |
| 2018/0186729 A1* | 7/2018 | Busch | ...................... | B01D 3/14 |

FOREIGN PATENT DOCUMENTS

| | | | | |
|---|---|---|---|---|
| WO | | 2012130788 A1 | 10/2012 | |
| WO | WO-2012130788 A1 * | | 10/2012 | ........... C07C 265/00 |

OTHER PUBLICATIONS

L. Cotarca et al., Phosgene, in Ullmann's Encyclopedia of Industrial Chemistry (2019) (Year: 2019).*

International Search Report, PCT/EP2018/066746, dated Oct. 24, 2018, Authorized officer: Thomas Straub.

* cited by examiner

ENERGY-EFFICIENT METHOD FOR PROVIDING A PURIFIED PHOSGENE VAPOR

CROSS-REFERENCE TO RELATED APPLICATIONS

This Application is a National Phase Application of PCT/EP2018/066746, filed Jun. 22, 2018, which claims priority to European Application No. 17178652.8, filed Jun. 29, 2017, each of which are being incorporated herein by reference.

FIELD OF THE INVENTION

The present invention relates to an energy-efficient process for providing purified phosgene vapor from chlorine and carbon monoxide. The invention further provides an apparatus for producing purified phosgene vapor and for the use of the purified phosgene vapor chemical synthesis.

BACKGROUND OF THE INVENTION

The continuous production of phosgene in what are called phosgene combiners is known and is described, for example, in "Ullmann's Encyclopedia of Industrial Chemistry", 7th edition 2012, volume 26, p. 625 ff (ch. 3, Production) Also described therein is a variant of phosgene generation in which the phosgene is generated in a first reaction step at elevated temperatures of 200 to 300° C. Owing to the unfavorable equilibrium position at this high temperature, there follows a second reaction step at lower temperature. The reaction is effected at standard pressure or slightly elevated pressure, and the gaseous phosgene is either used directly or first condensed and/or absorbed in a solvent in order to produce phosgene solution.

DE3327274A1 likewise describes a two-stage process for generating phosgene, wherein the waste heat from the first process stage is utilized at high temperature (hot phosgene generation) to generate steam, and the exiting reaction gases are then cooled down to 50-120° C. before the conversion is completed in a further reaction stage at 50-100° C., such that the chlorine content in the crude phosgene falls to <50 ppm by volume.

In this way, it is possible to very efficiently produce phosgene containing only a small amount of chlorine. However, since carbon monoxide, also called CO hereinafter, is typically used in a stoichiometric excess for phosgene generation, the product stream from the phosgene combiners still contains in some cases considerable amounts of unconverted carbon monoxide.

EP 1 640 341 A2 or else DE 102007057462 A1 states that the excess of CO can be physically utilized and hence CO emissions can be reduced. For this purpose, the crude product exiting from the phosgene combiners is first subjected to a partial condensation, wherein phosgene is condensed and CO-containing residual gases are separated off. These residual gases, with supply of further chlorine, are converted to further phosgene in at least one recombiner and then the phosgene produced in the recombiner is also condensed in at least one recondenser and uncondensable residual gases are removed.

U.S. Pat. No. 4,231,959 describes a similar process. However, the uncondensable residual gas from the condensation here is not converted in a recombiner but recycled into the actual phosgene combiner.

This actually requires an increase in pressure, for which it is possible to use a mechanical compressor or a jet pump, for example, in which one of the fresh gases, for example, is used as motive medium.

A disadvantage of these processes for phosgene production is that either gaseous phosgene with considerable proportions of inert CO is obtained as a product (Ullmann) or else phosgene is obtained as a liquid stream (EP '341, DE '462 and U.S. Pat. No. '959), in which case high cooling power is required for the condensation, and at a technically unfavorable temperature level owing to the low boiling point of phosgene. U.S. Pat. No. '959 mentions, for example −20° C. to −30° C. at 1.5 kg/cm² to 4.25 kg/cm² for complete condensation. Moreover, in many nowadays customary industrial applications of phosgene, one example of which is the gas phase phosgenation of amines for preparation of isocyanates, the phosgene is used as a gas, and so the liquid phosgene has to be evaporated again later.

WO 2012/130788 A1 discloses a process for preparing isocyanates, in which phosgene-containing reaction mixture from the gas phase synthesis of carbon monoxide and chlorine to give phosgene is separated into two substreams, one of which is liquid and contains <1% by weight of carbon monoxide, and the other is gaseous and contains >10% by weight of carbon monoxide. It is also stated that the liquid stream can be compressed by means of a pump, such that the direct coupling of the pressure level in the phosgene generation and the gas phase phosgenation is eliminated. In addition, this document also mentions various modes of energy integration. For example, the first phosgene stream having a low carbon monoxide content can be used as coolant for the phosgene synthesis, in which case it is evaporated and optionally also superheated. Even though a safety-related advantage over cooling of the phosgene reactor with water is mentioned, there are in fact also reservations against the procedure described. The use of phosgene on the shell side of a heat exchanger (e.g. a phosgene combiner) harbors the risk of leakage to the outside, and so such a use is not very advisable, and even in the compressing of liquid phosgene by means of a pump there is the risk of leaks.

Furthermore, WO 2012/130788 A1 also describes the option of coupling the partial condensation step and the evaporation step for heat purposes if the evaporation is executed at a lower pressure level than the condensation. It is merely mentioned that a pressure differential of more than 10 mbar is preferred without naming any resultant advantages at all.

For the second, carbon monoxide-rich stream, it is mentioned that it is preferably recycled into the phosgene generation. In this way, CO is physically utilized, but has to be compressed for that, and it is possible for components, especially oxygen, to accumulate in the circuit that is then closed, and so a substream is generally discharged and disposed of.

BRIEF DESCRIPTION OF THE FIGURES

The present invention will now be described for purposes of illustration and not limitation in conjunction with the figures, wherein.

DETAILED DESCRIPTION OF THE INVENTION

Figure 1:
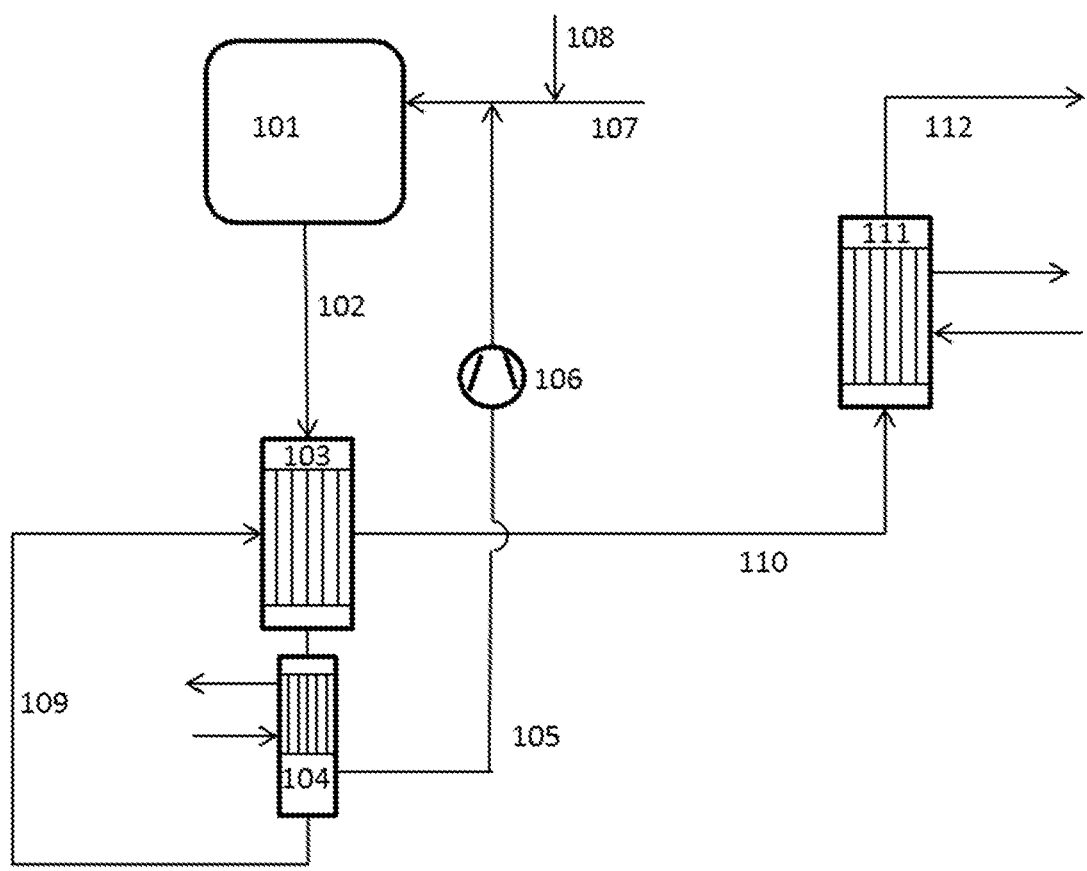
FIG. 1 shows the phosgene purification of WO2012130788A1.

It was therefore an object of the present invention, in a very efficient and reliable manner, to provide a low-CO phosgene gas for further use in chemical synthesis, wherein it is possible to dispense with further pumps and evaporation steps for the phosgene.

This object was achieved by a process for producing purified phosgene vapor, comprising the steps of
1) providing a gas stream comprising phosgene and carbon monoxide, obtainable from the reaction of chlorine with carbon monoxide,
2) condensing the gas stream in one or more stages and removing uncondensable residual gases,
3) evaporating the liquid phosgene obtained in step 2) in one or more stages and optionally superheating the phosgene vapor generated,
wherein there is energy integration between one or more of the condensation stages of step 2) and one or more of the evaporation stages in step 3) and the pressure in the last condensation stage is between ≥0.2 and ≤6.0 bar higher than in the first evaporation stage.

In the present context, the term "energy integration" is understood to mean that the energy released in the condensation is at least partly utilized directly and/or indirectly for evaporation.

In the present context, the pressures reported in the unit "bar" can be converted using the commonly known conversion factors to the corresponding values in the unit Pascal ("Pa"): 1 bar is equal to 100 000 Pa.

In a first preferred embodiment, the pressure in the last condensation stage is between ≥0.3 and ≤4.5 bar, preferably between ≥0.5 and ≤3.0 bar, more preferably between ≥0.8 and ≤2.5 bar and most preferably between ≥1.0 and ≤2.5 bar higher than in the first evaporation stage.

The gas stream is preferably provided in step 1) from a production process utilizing some of the heat of reaction for generation of steam (hot phosgene generation). Such a process is described in detail, for example, in DE3327274A1 or DE 102007057462 A1. In a further preferred embodiment, the gas stream provided, as well as phosgene, contains ≥1% by volume to ≤20% by volume, preferably ≥2% by volume to ≤12% by volume and more preferably ≥3% by volume to ≤10% by volume of CO. The CO content can be ascertained, for example, by means of IR photometry. This is because an excess of CO in the phosgene synthesis is intended to achieve a maximum conversion of chlorine. Chlorine itself is then usually present only in traces of <50 ppm by volume. The pressure in the phosgene generation is preferably chosen at such a high level that there is a pressure gradient from the phosgene combiners through the condensation stage and evaporation stage to the later use in the chemical synthesis.

In a further preferred embodiment, the condensable constituents of the crude phosgene provided in step 1) are at least partly condensed in step 2) in a first condenser at a pressure between ≥2.0 bar(a) and ≤10.0 bar(a), preferably between ≥2.5 bar(a) and ≤6.0 bar(a) and most preferably between ≥3.0 bar(a) and ≤5.0 bar(a). The person skilled in the art will see that, in the case of a lower pressure in the condensation, the pressure differential achievable between condensation and evaporation will of course also be limited, and so, in this case, will if anything be in the lower range of the preferred ranges specified above in each case.

A suitable condenser for this step is a heat exchanger, preferably a shell and tube heat exchanger. A preferred material for the heat exchanger is stainless steel. In a preferred embodiment, the crude phosgene is in the tubes of the heat exchanger and a cooling medium is on the shell side. This embodiment minimizes the risk of escape of phosgene to the outside.

Preferably, the entire phosgene-containing process stream from this heat exchanger is guided into a further condenser in which a further condensation is effected. Examples of suitable heat exchangers for this further condensation step include those already described in the first condensation stage. The temperature in the last condensation stage is preferably between ≥−60° C. and ≤0° C., more preferably between ≥−35° C. and ≤−5° C. and most preferably between ≥−20° C. and ≤−10° C. Such a multistage process regime leads to a more stable process which is less prone to fluctuation. Furthermore, an at least two-stage condensation is helpful to start up the process and the energy integration of the invention and to ensure maximum condensation of the phosgene. The condensation preferably has two stages. In this way, the advantages mentioned can be implemented with low apparatus complexity.

In a further preferred embodiment of the process of the invention, the uncondensable residual gases from step 2) which preferably contain CO as the main constituent are subjected to further conversion to phosgene in at least one recombiner with chlorine. A recombiner is understood in the present context to mean a postreactor for further conversion of carbon monoxide and chlorine to phosgene. The main constituent of the residual gas is considered to be CO in the present context when no other compound assumes a higher molar proportion in the residual gas. The uncondensable residual gases preferably consist to an extent of ≥50 mol % of CO. The uncondensable residual gases are preferably taken from the condenser furthest downstream. Suitable recombiners are described, for example, in DE 102007057462 A1 paragraph [0011]. The CO content of the offgas from the second condenser is continuously monitored here and the amount of chlorine gas supplied for the recombination is controlled correspondingly such that there is a molar CO excess over chlorine of ≥1.5% to ≤20%, preferably ≥2% to ≤12%, in the gas mixture to the recombiner. The CO content can be monitored, for example, by means of IR photometry.

The liquid phosgene obtained in the condensers in step 2) is guided into the first evaporation stage, for example via a pipeline with a pressure-retaining valve. It is preferable here to keep the amount of liquid as small as possible in order not to unnecessarily increase the phosgene load in the plant. It is also advantageous to take the measures known to those skilled in the art in order to prevent breakthrough of gaseous phosgene into the evaporator. In a particularly preferred embodiment of the process of the invention, the apparatuses are arranged in spatial terms such that the pressure differential between the condensers and the evaporators is sufficient to convey the liquid phosgene into the evaporation stage.

Suitable evaporators in step 3) are the heat exchangers known from the art, preferably shell and tube heat exchangers, more preferably those made of stainless steel. The evaporation is effected at a pressure between ≥0.3 and ≤5.0 bar, preferably between ≥0.5 and ≤3.0 bar, more preferably between ≥0.8 and ≤2.5 bar and most preferably between ≥1.0 and ≤2.5 bar lower than the pressure on the crude phosgene side of the first condenser. This pressure differential of the invention firstly assures a sufficient temperature difference between condensation temperature and evaporation temperature, such that the energy integration can be effected in an efficient manner and with technically viable heat transfer areas. Secondly, the pressure in the upstream phosgene generation is thus limited at the upper end, which in turn limits the amount of phosgene being handled in the plant, limits the expenditure for the compression of the chlorine and carbon monoxide reactants, prevents occurrence of liquid in the phosgene combiners and dispenses with any additional compression of the gaseous crude phosgene stream prior to the condensation. Instead, in the process of the invention, the pressure typically available in the reactants for phosgene generation, chlorine and carbon monoxide, is sufficient to convey the gaseous and liquid phosgene streams to the desired sites as far as the downstream processes without requiring additional compression steps.

In a further preferred embodiment, the pressure in the evaporation stage (step 3)) is ≥1.5 bar(a), preferably ≥1.8 bar(a), more preferably ≥2.0 bar(a) and most preferably above ≥2.5 bar(a). In this way, for many applications of the phosgene vapor in chemical synthesis, it is possible to dispense with compression of the phosgene, whether in vaporous or liquid form before the evaporation. In a preferred embodiment of the invention, the phosgene is evaporated on the tube side of a shell and tube heat exchanger. The pressure gradient of the invention can readily be established, for example, via closed-loop control valves or pressure-retaining valves in the respective outlets for the gases and via a pressure-retaining valve between condensation (step 2)) and evaporation (step 3)).

The energy integration of the invention can then be effected, for example, in that a condensation stage and an evaporation stage are integrated in a single apparatus, for example a shell and tube heat exchanger. In this case, it is preferable to allow the condensation to proceed at higher pressure in the tubes, while the evaporation proceeds at lower pressure on the shell side. The direct energy transfer makes such a procedure particularly efficient.

In a preferred embodiment, the energy integration is effected by means of a heat transfer circuit between at least one condenser from step 2) and at least one evaporator from step 3). In this case, condensation and evaporation are conducted on the tube side in each of two separate apparatuses, for example shell and tube heat exchangers, and the energy integration is accomplished via a heat transfer medium which is circulated between the two apparatuses. The advantage of such an embodiment is that the risk of phosgene leakage to the outside is reduced without significantly lowering the efficiency compared to the procedure mentioned in the above paragraph. Heat transfer media used are preferably anhydrous substances that have a low viscosity even at low temperatures down to about −20° C. and remain efficiently pumpable. A preferred heat transfer medium is chlorobenzene. In a preferred embodiment, the heat transfer medium is circulated by means of a pump between the heat exchangers for condensation and for evaporation. In an alternative embodiment, the inlet of the heat transfer medium to the condenser is additionally provided with a means of cooling and/or the feed to the evaporator with a means of heating. This is advantageous especially in a single-stage condensation or evaporation in order to start up the process and the energy integration of the invention and to assure very substantial condensation/evaporation of the phosgene.

In a development of the invention, a superheating stage may follow, in which the phosgene vapor is superheated in a heat exchanger. Here too, energy integration is an option. If, in the preferred embodiment, the gas stream for step 1) is provided from a hot phosgene generation, the above-described cooling of the reaction gases leaving the reactor, for avoidance of a chlorine-iron fire, can provide sufficient energy for the superheating. Preferably, the energy integration is again effected here via circulation of a heat transfer medium. More preferably, the heat transfer medium is anhydrous, and it is most preferably chlorobenzene. In order to minimize the complexity of the process, it is advantageous to use the same heat transfer medium as energy carrier for the energy integrations described in the two preceding paragraphs.

According to the quality demand (CO content) on the purified phosgene vapor produced by the process of the invention, it is possible to choose between different embodiments of the invention. If relatively high contents of CO are permissible, it is possible, according to the CO excess chosen, to combine the phosgene stream obtained from the recombination directly with the phosgene vapor from the evaporator or, if appropriate, superheater. In the preferred embodiment with a recombiner for the residual gases, the effect of a smaller CO excess in the recombiner is a further-reduced CO content of the phosgene vapor produced.

In the event of elevated quality demands, there is preferably also a condensation (recondensation) of the reaction gas exiting from the recombiner, as described in DE102007057462 paragraph [0030 ff.]. The liquid phosgene obtained in this recondensation is preferably added to the condensed phosgene obtained in step 2). This addition is preferably effected downstream of the pressure-retaining unit, where the evaporator pressure is already lower, and so no pump is required here either for conveying of the phosgene.

Alternatively, it is even possible by the process of the invention with recombiner to provide phosgene vapor at various quality levels. This may be advantageous when various downstream processes with different quality demands, for example on the CO content of the phosgene, are to be served. For example, it is possible to take a substream or the entirety of the phosgene purified by condensation and evaporation for a process with high demands and to use any remaining residual stream together with the less pure phosgene stream from the recombiner for another, less demanding process.

The present invention further provides an apparatus for producing purified phosgene vapor from the reaction of chlorine with carbon monoxide, comprising a condensation unit for partial compensation of a gas stream comprising phosgene and carbon monoxide, having at least
a first inlet for the gas stream comprising phosgene and carbon monoxide and
a first outlet for uncondensed gases, an evaporation unit for evaporating the liquid condensed in the condensation unit, having at least
a second outlet for a gaseous phosgene stream, a connecting conduit that departs from the condensation unit and opens into the evaporation unit for conveying the liquid condensed in the condensation unit and a device for transfer of heat from the condensation unit to the evaporation unit, comprising
at least one heat transfer surface which is formed by a wall common to the condensation unit and the evaporation unit or
at least one secondary circuit having at least one common wall with each of the two spaces and set up to accommodate a heat transfer medium,
characterized in that the condensation unit is set up such that a positive pressure relative to the evaporation unit of ≥0.2 and ≤6.0 bar is attained.

The condensation unit is preferably set up such that the positive pressure relative to the evaporation unit reaches ≥0.3 and ≤4.5 bar, preferably between ≥0.5 and ≤3.0 bar, more preferably between ≥0.8 and ≤2.5 bar and most preferably between ≥1.0 and ≤2.5 bar.

The apparatus of the invention can be used, in an energy-efficient manner, to prepare purified phosgene vapor from a gas stream comprising phosgene and carbon monoxide.

In a first preferred embodiment, a first pressure-retaining device is assigned to the connecting conduit of the purifying apparatus of the invention. This device serves simultaneously to homogenize the flow from the condensation unit to the evaporation unit and to prevent the breakthrough of the uncondensable gases.

In a further preferred embodiment of the purifying apparatus of the invention, a second pressure-retaining device is assigned to the first outlet for uncondensed gases.

In a further preferred embodiment of the purifying apparatus of the invention, a third pressure-retaining device is assigned to the second outlet for a gaseous phosgene stream.

Pressure-retaining devices used both for the process of the invention and for the apparatus of the invention may, for example, be closed-loop control valves, water traps, siphons, perforated plates, throttle valves, overflow valves, pressure-retaining valves and or a skillful three-dimensional arrangement of the apparatuses. Pressure-retaining devices used are preferably closed-loop control valves, where the control circuits preferably include pressure sensors. This offers the advantage that the apparatus of the invention enables exact control of the pressure in the condensation unit and evaporation unit. Moreover, the use of closed-loop control valves offers the advantage that, by contrast with water traps or siphons, only a low liquid level, if any, is required, such that the amount of phosgene being handled in the apparatus is not unnecessarily increased.

In a further preferred embodiment, the condensation unit and the evaporation unit are each the tube side of one or more shell and tube heat exchangers.

It is particularly preferable here that the heat transfer device comprises one or more conduits and at least one forced conveying unit, these being arranged, with inclusion of the shell sides of the shell and tube heat exchangers, in such a way as to result in a circuit in which a heat transfer medium can be circulated.

Phosgene is important, for example, for isocyanate production from amines; thus, the present invention further provides for the use of the purified phosgene vapor from the process of the invention or from the apparatus of the invention for phosgenation of amines in the gas phase. The gas phase phosgenation of amines is known, for example, from EP 0 289 840 A1.

The present invention is elucidated in detail with reference to the figures and examples which follow, but without being restricted thereto. It is possible for the person skilled in the art, for example by increasing the pressure differential between condensation and evaporation or else via a higher heat transfer area, to maximize the energy saving by the energy integration.

FIG. 1 describes one embodiment of the phosgene purification described in WO2012130788A1. A gaseous crude phosgene stream (102) containing not only phosgene but also excess carbon monoxide exits from the phosgene combiner (101). The phosgene from this stream is partly condensed in two successive heat exchangers (103, 104). The gaseous, CO-rich stream (105) is compressed in a compressor (106) and guided back into the phosgene generator (101) together with chlorine (107) and fresh CO (108). The liquid phosgene stream (109) serves as coolant for the heat exchanger (103) in which the phosgene has been condensed beforehand. The (partly) evaporated phosgene stream (110) is superheated in a further heat exchanger (111) and then supplied as stream (112) to a gas phase phosgenation of amines.

Figure 2:
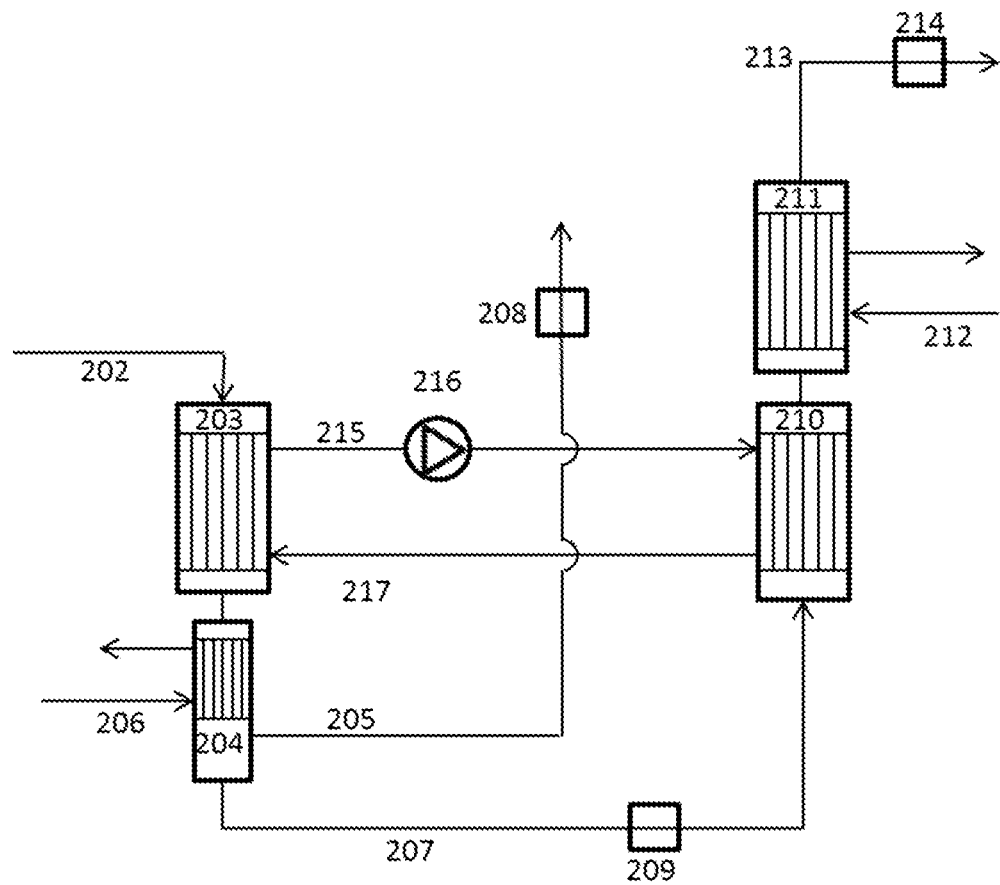
FIG. 2 illustrates a preferred embodiment of the process of the invention.

FIG. 2 describes a preferred embodiment of the process of the invention. The crude phosgene stream from the phosgenation (202) is partly condensed in two successive heat exchangers (203, 204), with cooling of the heat exchanger (204) by means of monochlorobenzene (206) at −13° C. The uncondensable, CO-rich gas stream (205) is removed via a pressure-retaining valve (208) and sent, for example, to an offgas treatment. The liquid phosgene stream (207) is expanded via a pressure-retaining device (209) and then evaporated and superheated in two successive heat exchangers (210, 211). The heat exchanger (211) is heated here with hot monochlorobenzene (212). The superheated phosgene stream (213) is sent to its downstream use via a closed-loop control valve (214) that also serves to control the pressure for the evaporation step. The heat exchangers (203) and (204), on the shell side, are part of a common heat transfer circuit. In the heat exchanger (203), heat transfer medium (215) heated up by the condensation is conveyed to the heat exchanger (210) by means of a pump (216). It releases heat to the evaporating phosgene and is cooled down therein. The cooled heat transfer medium (217) is then guided back to the heat exchanger (203). Alternatively, it is of course likewise conceivable to integrate the pump (216) into the cold heat carrier stream (217) rather than into the hot heat carrier stream (215).

Figure 3:
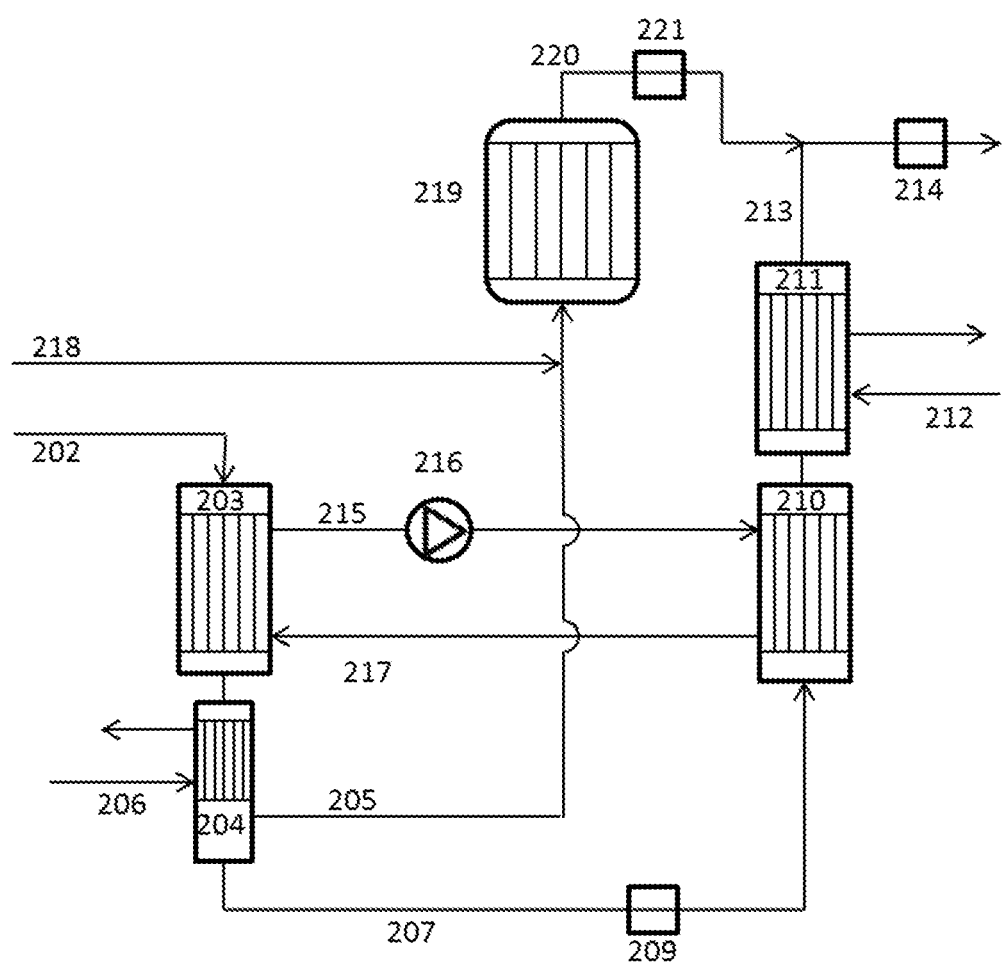
FIG. 3 provides another embodiment of the process of the invention using a phosgene recombiner.

FIG. 3 describes a further preferred embodiment of the process of the invention using a phosgene recombiner. In this embodiment, the uncondensable CO-rich gas stream (205) is admixed with chlorine (218) and converted in a recombiner (219) to further phosgene (220), which is then supplied via a closed-loop control valve (221) to the superheated phosgene stream (213).

FIG. 2 and FIG. 3 also describe preferred configurations of the apparatus of the invention for purifying phosgene. Therefore, the devices, conduits and apparatuses mentioned in FIG. 2 and FIG. 3, including their reference numerals, are likewise part of these preferred configurations of the apparatus of the invention.

EXAMPLES

The examples are model calculations that were produced by means of Aspen Plus® V8.8. This was done using the physical data for CO and phosgene that are included in the software (Wilson/ideal gas model using the AVP88-PURE24 database available in Aspen Plus®).

Figure 4:
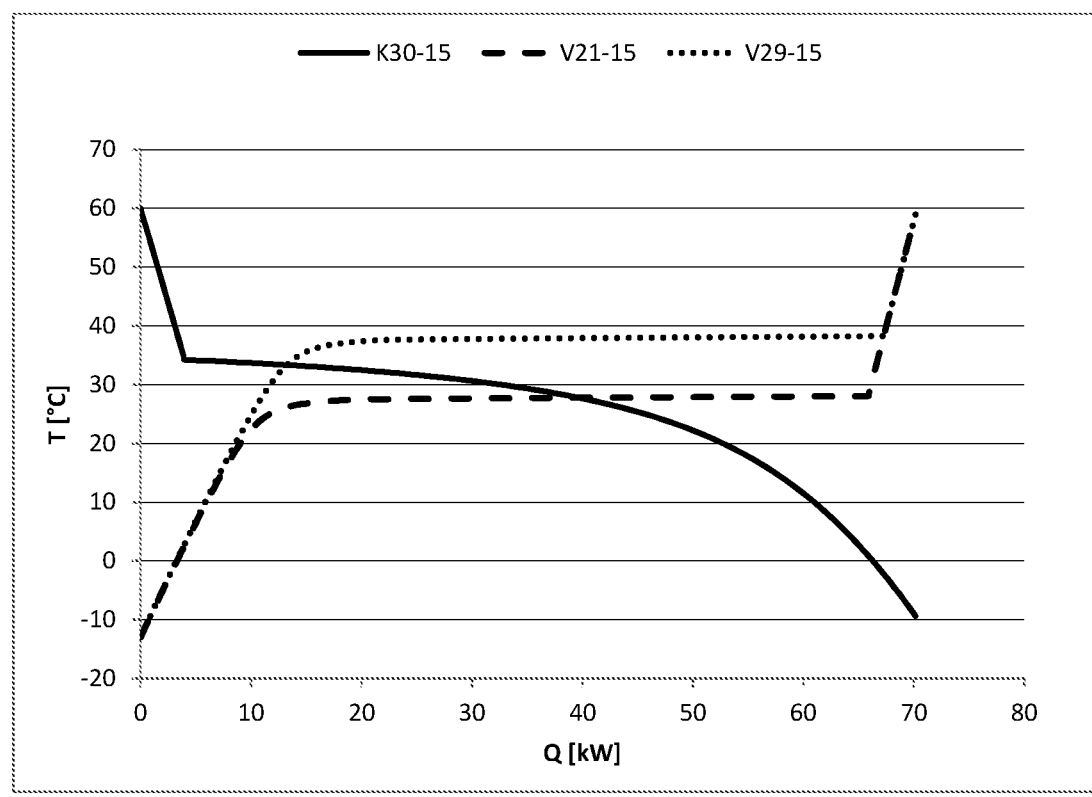
FIG. 4 shows the cooling and heating curves from examples 2 to 4.
Figure 5:
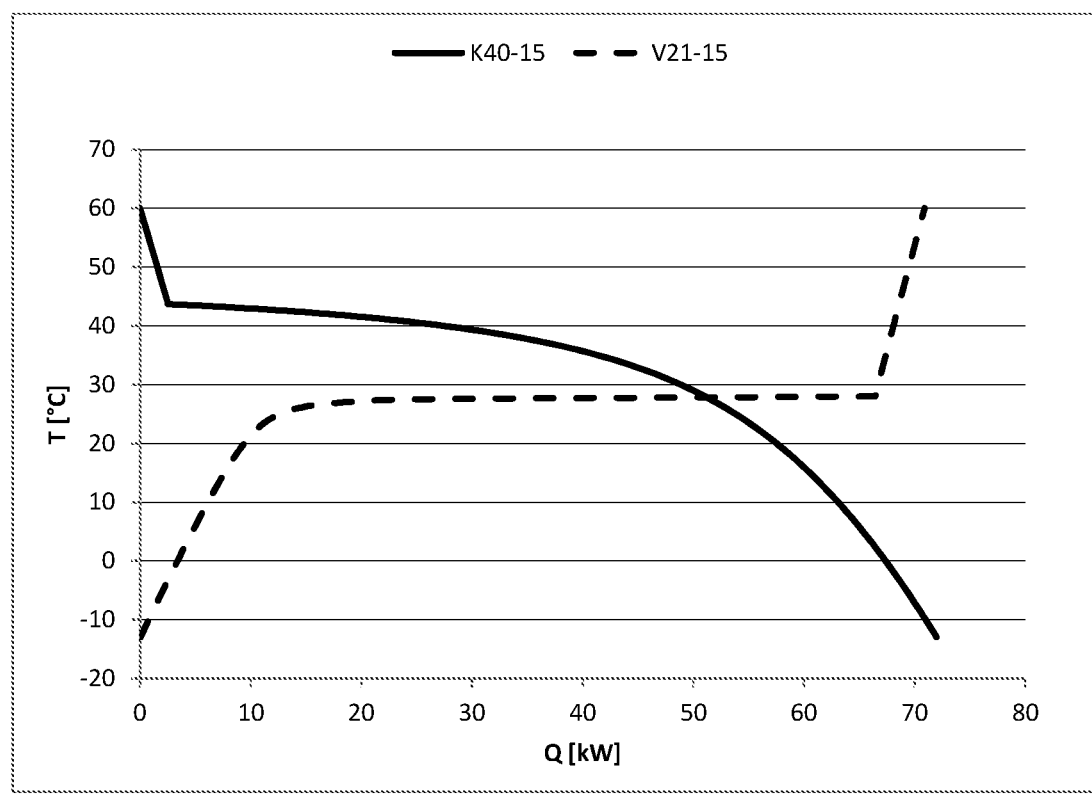
FIG. 5 illustrates the cooling and heating curves from examples 5 and 6.
Figure 6:
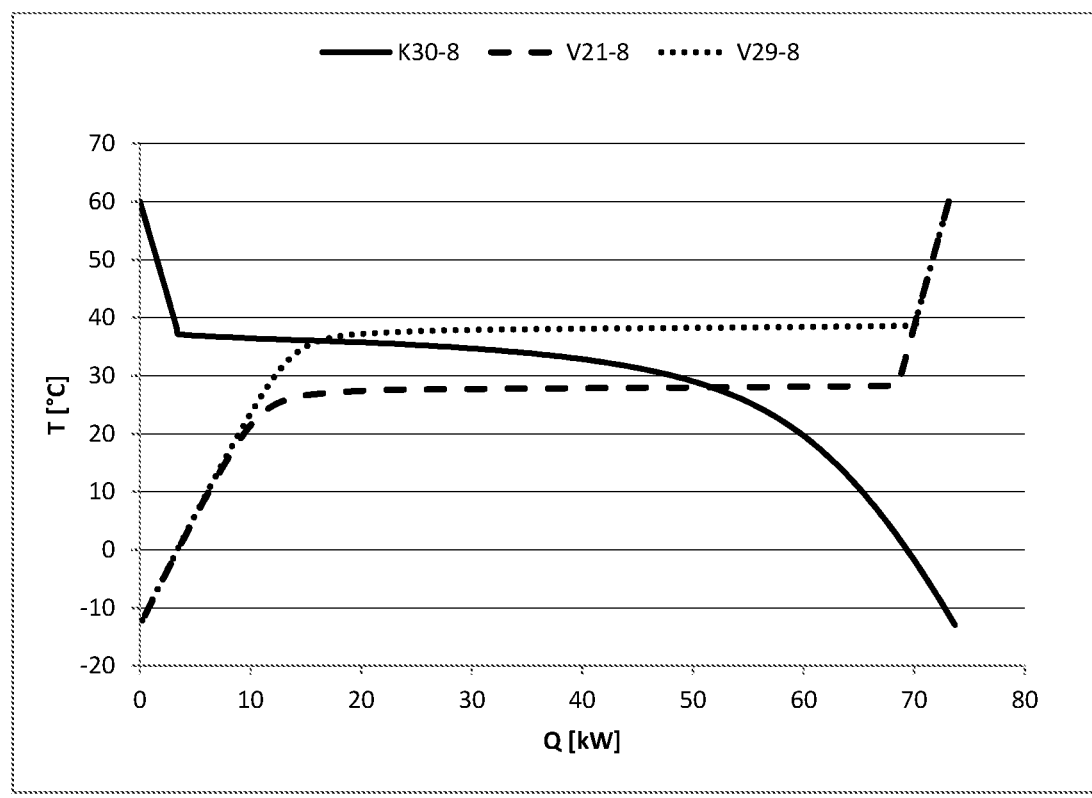
FIG. 6 shows the cooling and heating curves from examples 7 to 9.

The cooling curves for condensation processes and heating curves for the evaporation processes that are mentioned in the examples are shown in FIGS. 4, 5 and 6. The figures show:

FIG. 4 the cooling and heating curves from examples 2 to 4,

FIG. 5 the cooling and heating curves from examples 5 and 6 and

FIG. 6 the cooling and heating curves from examples 7 to 9.

In each case, the cooling power (condensation) or heating power (evaporation) is plotted on the x axis, both types of power being given the same sign for better clarity. On the y axis, by contrast, the temperature in ° C. is plotted in each case.

Example 1 (Dew Points of Gaseous Mixtures of Carbon Monoxide and Phosgene)

In model calculations, gas mixtures consisting of 15 mol % of CO and 85 mol % of phosgene or 8 mol % of CO and 92 mol % of phosgene were cooled from 60° C. down to −13° C. The pressure was varied and the respective dew point was documented.

| Pressure [bar (a)] | Dew point 15% CO [° C.] | Dew point 8% CO [° C.] |
|---|---|---|
| 2 | 21.9 | 24.2 |
| 2.5 | 28.5 | 31.0 |
| 3 | 34.2 | 36.8 |
| 3.5 | 39.2 | 41.9 |
| 4 | 43.7 | 46.4 |
| 5 | 51.5 | 54.4 |
| 6 | 58.2 | 61.2 |
| 8 | 69.4 | 72.6 |
| 10 | 78.7 | 82.0 |

Example 2: (Condensation at 3.0 Bar(a); 15% CO)

A 900 kg/h stream of the abovementioned composition with 15 mol % of CO was cooled in a flash calculation at 3.0 bar(a) from 60° C. down to −13° C. and separated into a gaseous CO-rich stream and a liquid phosgene-rich stream. As shown in example 1, the condensation set in at a dew point of 34.2° C. For the cooling from 60° C. down to −13° C., a cooling power of 71.5 kW was required. Only a small portion of this energy was taken from the superheating of the gas stream. By far the greater portion comes from the condensation of the phosgene and does not accrue until temperatures below the dew point (see cooling curve K30-15 in FIG. 4). The liquid exit stream of 834 kg/h still contained about 0.4% CO.

Example 3 (Comparative Example: Evaporation of the Liquid Stream from Example 2 at a Pressure of 2.9 Bar(a), i.e. 100 Mbar Below the Pressure of the Condensation Stage)

The phosgene stream of 834 kg/h from example 2 that had been condensed at 3.0 bar(a) and −13° C. was subjected to another evaporation and superheating to 60° C., for which 70.3 kW of heating power was required. The evaporation was effected here at a pressure of 2.9 bar(a). The corresponding heating curve (V29-15 in FIG. 4) shows that the major portion of the evaporation energy is required at about 38° C. and hence above the dew point (34.2° C.) of the gas mixture of carbon monoxide and phosgene under these conditions. The evaporation is completed at about 38.2° C. (67.2 kW). It becomes clear from the comparison of the cooling curve of the phosgene/CO mixture at 3.0 bar(a) (K30-15 in FIG. 4) and the heating curve of the purified phosgene at 2.9 bar(a) (V29-15 in FIG. 4) that energy integration at the pressure differential chosen is unviable since fractions at best of the energy needed for the condensation/evaporation can be accounted for by the thermal coupling.

Example 4 (Inventive Example: Evaporation of the Liquid Stream from Example 2 at a Pressure of 2.1 Bar(a), i.e. 0.9 Bar Below the Pressure of the Condensation Stage)

The phosgene stream of 834 kg/h from example 2 that had been condensed at 3.0 bar(a) and −13° C. was subjected to another evaporation and superheating to 60° C., for which 70.3 kW of heating power was required. The evaporation was effected here at a pressure of 2.1 bar(a). The corresponding heating curve (V21-15 in FIG. 4) shows that the major portion of the evaporation energy is required at about 28° C. and hence below the dew point (34.2° C.) of the gas mixture of carbon monoxide and phosgene under these conditions. The evaporation is completed at about 28.1° C. (65.4 kW). It becomes clear that energy integration at the chosen pressure differential of 0.9 bar is viable since a significant portion of the cooling energy and heating energy required can be provided in each case via the heat of condensation or evaporation within the scope of the energy integration.

Example 5: (Condensation at 4.0 Bar(a); 15% CO)

A 900 kg/h stream of the abovementioned composition with 15 mol % of CO was cooled in a flash calculation at 3.0 bar(a) from 60° C. down to −13° C. and separated into a gaseous CO-rich stream and a liquid phosgene-rich stream. As shown in example 1, the condensation set in at a dew point of 43.7° C. For the cooling from 60° C. down to −13° C., a cooling power of 72.0 kW was required. Only a small portion of this energy was taken from the superheating of the gas stream. By far the greater portion comes from the condensation of the phosgene and does not accrue until temperatures below the dew point (see cooling curve K40-15 in FIG. 5). The liquid exit stream of 841 kg/h still contained about 0.4% CO.

Example 6 (Inventive Example: Evaporation of the Liquid Stream from Example 5 at a Pressure of 2.1 Bar(a), i.e. 1.9 Bar Below the Pressure of the Condensation Stage)

The phosgene Stream of 841 kg/h from example 3 that had been condensed at 4.0 bar(a) and −13° C. was subjected to another evaporation and superheating to 60° C., for which 70.9 kW of heating power was required. The evaporation was effected here at a pressure of 2.1 bar(a). The corresponding heating curve (V21-15 in FIG. 5) shows that the major portion of the evaporation energy is required at about 28° C. and hence below the dew point (34.2° C.) of the gas mixture of carbon monoxide and phosgene under these conditions. The evaporation is completed at about 28.0° C. (66.4 kW). It becomes clear that energy integration at the chosen pressure differential of 1.9 bar is viable since a significant portion of the cooling energy and heating energy required can be provided in each case via the heat of condensation or evaporation within the scope of the energy integration.

Example 7 (Condensation at 3.0 Bar(a); 8% CO)

A 900 kg/h stream of the abovementioned composition with 8 mol % of CO was cooled in a flash calculation at 3.0 bar(a) from 60° C. down to −13° C. and separated into a gaseous CO-rich stream and a liquid phosgene-rich stream. As shown in example 1, the condensation set in at a dew point of 36.8° C. For the cooling from 60° C. down to −13° C., a cooling power of 73.7 kW was required. Only a small portion of this energy was taken from the superheating of the gas stream. By far the greater portion comes from the condensation of the phosgene and does not accrue until temperatures below the dew point (see cooling curve K30-8 in FIG. 6). The liquid exit stream of 867 kg/h still contained about 0.4% CO.

Example 8 (Comparative Example: Evaporation of the Liquid Stream from Example 7 at a Pressure of 2.9 Bar(a), i.e. 100 Mbar Below the Pressure of the Condensation Stage)

The phosgene stream of 867 kg/h from example 7 that had been condensed at 3.0 bar(a) and −13° C. was subjected to another evaporation and superheating to 60° C., for which 73.1 kW of heating power was required. The evaporation was effected here at a pressure of 2.9 bar(a). The corresponding heating curve (V29-8 in FIG. 6) shows that the major portion of the evaporation energy is required at about 38° C. and hence above the dew point (36.8° C.) of the gas mixture of carbon monoxide and phosgene under these conditions. The evaporation is completed at about 38.2° C. (70.0 kW). It becomes clear from the comparison of the cooling curve of the phosgene/CO mixture at 3.0 bar(a) (K30-8 in FIG. 6) and the heating curve of the purified phosgene at 2.9 bar(a) (V29-8 in FIG. 6) that energy integration at the pressure differential chosen is unviable since fractions at best of the energy needed for the condensation/evaporation can be accounted for by the thermal coupling.

Example 9 (Inventive Example: Evaporation of the Liquid Stream from Example 7 at a Pressure of 2.1 Bar(a), i.e. 0.9 Bar Below the Pressure of the Condensation Stage)

The phosgene stream of 867 kg/h from example 7 that had been condensed at 3.0 bar(a) and −13° C. was subjected to another evaporation and superheating to 60° C., for which 73.1 kW of heating power was required. The evaporation was effected here at a pressure of 2.1 bar(a). The corresponding heating curve (V21-8 in FIG. 6) shows that the major portion of the evaporation energy is required at about 28° C. and hence below the dew point (36.8° C.) of the gas mixture of carbon monoxide and phosgene. The evaporation is completed at about 28.0° C. (68.5 kW). It becomes clear that energy integration at the chosen pressure differential of 0.9 bar is viable since a significant portion of the cooling energy and heating energy required can be provided in each case via the heat of condensation or evaporation within the scope of the energy integration.

Example 10 (Comparative Example: Condensation at 9.0 Bar(a), Evaporation at 2.0 Bar(a))

This example in turn is based on a gas stream having a composition of 8 mol % of CO and 92 mol % of phosgene. The evaporation is to be effected at 2 bar(a). The pressure difference of 7 bar leads to a large temperature difference between condensation stage and evaporation stage and hence theoretically enables efficient energy integration. However, this procedure is associated with considerable disadvantages. It can be inferred from the correlation between pressure and dew point described in example 1 that a pressure of 9 bar(a) in the condensation stage is associated with a dew point of about 78° C. With smaller excesses of CO, the dew point actually rises even further. Since condensation in the upstream phosgene combiners should be avoided at all costs, these have to be operated at elevated temperatures outside the known preferred ranges (cf. DE '462, paragraph 0025). The consequence is an undesirably elevated chlorine content in the phosgene. Alternatively, the phosgene stream could be compressed between the phosgene generation and the condensation, but this requires energy and apparatuses for the compression and increases the risk of leakage. In addition, measures would have to be taken to counter uncontrolled condensation during the compression. Such a great pressure difference between condensation stage and evaporation stage is thus undesirable.

Various aspects of the subject matter described herein are set out in the following numbered clauses:

Clause 1. A process for producing purified phosgene vapor, comprising the steps of 1) providing a gas stream comprising phosgene and carbon monoxide, obtainable from the reaction of chlorine with carbon monoxide, 2) condensing the gas stream in one or more stages and removing uncondensable residual gases, 3) evaporating the liquid phosgene obtained in step 2) in one or more stages and optionally superheating the phosgene vapor generated, wherein there is energy integration between one or more of the condensation stages of step 2) and one or more of the evaporation stages in step 3) and the pressure in the last condensation stage is between ≥0.2 and ≤6.0 bar higher than in the first evaporation stage.

Clause 2. The process as in Clause 1, characterized in that the pressure in the last condensation stage is between ≥0.3 and ≤4.5 bar, preferably between ≥0.5 and ≤3.0 bar, more preferably between ≥0.8 and ≤2.5 bar and most preferably between ≥1.0 and ≤2.5 bar higher than in the first evaporation stage.

Clause 3. The process as in either of Clauses 1 and 2, characterized in that the gas stream provided in step 1), as well as phosgene, contains ≥1% by volume to ≤20% by volume, preferably ≥2% by volume to ≤12% by volume and more preferably ≥3% by volume to ≤10% by volume of CO.

Clause 4. The process as in any of Clauses 1 to 3, characterized in that the condensation in step 2) is effected at a pressure between ≥2.0 bar(a) and ≤10.0 bar(a), preferably between ≥2.5 bar(a) and ≤6.0 bar(a) and more preferably between ≥3.0 bar(a) and ≤5.0 bar(a).

Clause 5. The process as in any of Clauses 1 to 4, characterized in that the condensation in step 2) is effected in at least 2 stages, where the last stage is implemented between ≥−60° C. and ≤0° C., preferably between ≥−35° C. and ≤−5° C. and more preferably between ≥−20° C. and ≤−10° C.

Clause 6. The process as in any of Clauses 1 to 5, characterized in that the pressure in the evaporation in step 3) is above 1.5 bar(a), preferably ≥1.8 bar(a), more preferably above ≥2.0 bar(a) and most preferably above ≥2.5 bar(a).

Clause 7. The process as in any of Clauses 1 to 6, characterized in that the uncondensable residual gases from step 2) are subjected to further conversion to phosgene in at least one recombiner with chlorine.

Clause 8. The process as in any of Clauses 1 to 7, characterized in that the energy integration is effected by means of a heat transfer circuit between at least one condenser from step 2) and at least one evaporator from step 3).

Clause 9. An apparatus for producing purified phosgene vapor from the reaction of chlorine with carbon monoxide, comprising —a condensation unit for partial compensation of a gas stream comprising phosgene and carbon monoxide, having at least •a first inlet for the gas stream comprising phosgene and carbon monoxide and •a first outlet for uncondensed gases, —an evaporation unit for evaporating the liquid condensed in the condensation unit, having at least •a second outlet for a gaseous phosgene stream, —a connecting conduit that departs from the condensation unit and opens into the evaporation unit for conveying the liquid condensed in the condensation unit and —a device for transfer of heat from the condensation unit to the evaporation unit, comprising •at least one heat transfer surface which is formed by a wall common to the condensation unit and the evaporation unit or •at least one secondary circuit having at least one common wall with each of the two spaces and set up to accommodate a heat transfer medium, characterized in that the condensation unit is set up such that a positive pressure relative to the evaporation unit of ≥0.2 and ≤6.0 bar is attainable.

Clause 10. The apparatus as in Clause 9, characterized in that a first pressure-retaining device is assigned to the connecting conduit.

Clause 11. The apparatus as in Clause 9 or 10, characterized in that a second pressure-retaining device is assigned to the first outlet for uncondensed gases.

Clause 12. The apparatus as in any of Clauses 9 to 11, characterized in that a third pressure-retaining device is assigned to the second outlet for a gaseous phosgene stream.

Clause 13. The apparatus as in any of Clauses 9 to 12, characterized in that the condensation unit and the evaporation unit are each the tube side of one or more shell and tube heat exchangers.

Clause 14. The apparatus as in Clause 13, characterized in that the heat transfer device comprises multiple conduits and at least one forced conveying unit, these being arranged, with inclusion of the shell sides of the shell and tube heat exchangers, in such a way as to result in a circuit in which a heat transfer medium can be circulated.

Clause 15. The use of the purified phosgene vapor produced by a process as in any of Clauses 1 to 8 for phosgenation of amines in the gas phase.

The invention claimed is:

1. A process for producing purified phosgene vapor, comprising the steps of
1) providing a gas stream comprising phosgene and carbon monoxide, obtained from the reaction of chlorine with carbon monoxide,
2) condensing the gas stream in one or more stages and removing uncondensable residual gases,
3) evaporating the liquid phosgene obtained in step 2) in one or more stages and optionally superheating the phosgene vapor generated,
wherein there is energy integration between one or more of the condensation stages of step 2) and one or more of the evaporation stages in step 3) and the pressure in the last condensation stage is between ≥0.2 and ≤6.0 bar higher than in the first evaporation stage.

2. The process as claimed in claim 1, wherein the pressure in the last condensation stage is between ≥0.3 and ≤4.5 bar, higher than in the first evaporation stage.

3. The process as claimed in claim 1, wherein the gas stream provided in step 1), as well as phosgene, contains ≥1% by volume to ≤20% by volume, of CO.

4. The process as claimed in claim 1, characterized in that the condensation in step 2) is effected at a pressure between ≥2.0 bar(a) and ≤10.0 bar(a), preferably between ≥2.5 bar(a) and ≤6.0 bar(a) and more preferably between ≥3.0 bar(a) and ≤5.0 bar(a).

5. The process as claimed in claim 1, wherein the condensation in step 2) is effected in at least 2 stages, where the last stage is implemented between ≥−60° C. and ≤0° C.

6. The process as claimed in claim 1, wherein the pressure in the evaporation in step 3) is above 1.5 bar(a).

7. The process as claimed in claim 1, wherein the uncondensable residual gases from step 2) are subjected to further conversion to phosgene in at least one recombiner with chlorine.

8. The process as claimed in claim 1, wherein the energy integration is effected by means of a heat transfer circuit between at least one condenser from step 2) and at least one evaporator from step 3).

9. An apparatus for producing purified phosgene vapor from the reaction of chlorine with carbon monoxide, comprising
a condensation unit for partial condensation of a gas stream comprising phosgene and carbon monoxide, having at least
a first inlet for the gas stream comprising phosgene and carbon monoxide and
a first outlet for uncondensed gases,
an evaporation unit for evaporating the liquid condensed in the condensation unit, having at least
a second outlet for a gaseous phosgene stream,
a connecting conduit that departs from the condensation unit and opens into the evaporation unit for conveying the liquid condensed in the condensation unit and
a device for transfer of heat from the condensation unit to the evaporation unit, comprising
at least one heat transfer surface which is formed by a wall common to the condensation unit and the evaporation unit or
at least one secondary circuit having at least one common wall with each of the condensation unit and the evaporation unit and set up to accommodate a heat transfer medium,
wherein the condensation unit is set up such that a positive pressure relative to the evaporation unit of ≥0.2 and ≤6.0 bar is attained.

10. The apparatus as claimed in claim 9, wherein a first pressure-retaining device is assigned to the connecting conduit.

11. The apparatus as claimed in claim 9, wherein a second pressure-retaining device is assigned to the first outlet for uncondensed gases.

12. The apparatus as claimed in claim 9, wherein a third pressure-retaining device is assigned to the second outlet for a gaseous phosgene stream.

13. The apparatus as claimed in claim 9, wherein the condensation unit and the evaporation unit are each the tube side of one or more shell and tube heat exchangers.

14. The apparatus as claimed in claim 13, wherein the heat transfer device comprises multiple conduits and at least one forced conveying unit, these being arranged, with inclusion of the shell sides of the shell and tube heat exchangers, in such a way as to result in a circuit in which a heat transfer medium can be circulated.

* * * * *